United States Patent [19]

Dickson

[11] 4,149,986

[45] Apr. 17, 1979

[54] TOILET BOWL CLEANER

[76] Inventor: David J. Dickson, 8216 Ardmore Ave., Wyndmoor, Pa. 19118

[21] Appl. No.: 848,108

[22] Filed: Nov. 3, 1977

[51] Int. Cl.$^2$ .................. C11D 3/04; C11D 7/10; C11D 9/30
[52] U.S. Cl. .................. 252/108; 252/89 R; 252/132; 252/541
[58] Field of Search .................. 4/222, 228, 231; 252/89, 117, 132, 541, 542, 108; 210/64

[56] References Cited

U.S. PATENT DOCUMENTS 4,119,578  10/1978  Daeninckx et al. .................. 252/548

FOREIGN PATENT DOCUMENTS 48-44334  12/1973  Japan.

Primary Examiner—P. E. Willis, Jr.
Attorney, Agent, or Firm—Steele, Gould & Fried

[57] ABSTRACT

A toilet bowl cleaner comprising sodium sulphate, urea, a surfactant, water, sodium stearate and a water soluble dye is disclosed.

3 Claims, No Drawings

TOILET BOWL CLEANER

BACKGROUND OF THE INVENTION

Toilet bowl cleaners which are inserted in toilet tanks or toilet bowls have become commonplace. Typically, these bowl cleaners are in block or cake form and contain a surfactant and a water soluble dye in a carrier. The surfactant serves as the cleaning agent in the sense that it serves to prevent foreign matter from accumulating on the vitreous surfaces of the toilet bowl. From a psychological point of view, the dye is perhaps the most important component of toilet bowl cleaners since it imparts color to bowl water which serves as an indicator that the cleaner is functioning. The carrier serves its named function and also aids in controlling the rate and uniformity of solution of the surfactant and dye in tank or bowl waters.

There are two basic types of solid bowl cleaners sold commercially today. One consists of a mixture of surfactant and sodium sulphate with dye and other minor components. A second consists of a mixture of surfactant, urea, water soluble dye and other minor components. A third type of solid bowl cleaner could consist of surfactant and dye, however, such a composition would be excessively expensive in view of the relatively high cost of surfactant. Typical solid toilet bowl cleaner formulations of the foregoing types are exemplified by the copies of product data sheets from GAF Corporation, Union Carbide Corporation and Thompson-Hayward Chemical Company which are submitted with this application. Other solid toilet bowl cleaner compositions are described in U.S. Pat. Nos. 3,545,014; 3,760,429; 3,766,576 and 3,943,244, copies of which are submitted with this application.

DETAILED DESCRIPTION OF THE INVENTION

The present invention relates to a toilet bowl cleaner comprising from about 50% to about 60% sodium sulphate, from about 17% to about 24% urea, from about 8% to about 20% surfactant, from about 8% to about 11% water, from about 0.25% to about 2% sodium stearate, and from about 1% to about 2% water soluble dye, said percentages being by weight, based on the weight of the composition.

As mentioned, the surfactant serves as the cleaning agent in the new toilet bowl cleaner. A variety of surfactant materials may be used, however, nonionic primary alcohol ethoxylates such as those commercially available from Union Carbide or GAF Corp. under their respective trademarks Tergitol or Igepal are preferred. Generally, the surfactant will be in the form of a viscous oil rather than a low melting wax, but both liquid and solid surfactants may be used.

Sodium sulphate, sodium stearate and urea are used in their commercially available forms, and are not required to have special properties or characteristics.

Any water soluble dye may be used in the toilet bowl cleaner composition, however, usually a blue dye is selected as consumers have shown preference for blue color in bowl water.

In a preferred embodiment the toilet bowl cleaner of the invention comprises about 55% sodium sulphate, about 23% urea, about 10% surfactant, about 10% water, about 0.4% sodium stearate, and about 1.3% dye, said percentages being by weight, based on the weight of the composition. In addition, minor amounts of silicone, on the order of 0.1%, and an odorant such as methyl salicylate (0.4%) may be included in the bowl cleaner composition, although their presence is optional.

The toilet bowl cleaner of this invention has many advantages over previously known compositions. Most significant of these is the exceptionally greater life of the product. The longer life, measured in terms of number of flushes per ounce of bowl cleaner unit, is due to a generally slow rate of dissolution of the composition and its density which permits a significantly greater weight of bowl cleaner to be packed in conventional sized containers. In the latter respect, conventional size containers hold approximately 9 ounces of bowl cleaner composition and containers of larger size are thought to be too large for convenient placement in toilet tanks or bowls. The composition of this invention has sufficient density so that it is possible to include as much as 13 ounces of bowl cleaner in a standard 9 ounce container.

The slow rate of dissolution and increased density of the bowl cleaner composition are thought to be the result of combining both sodium sulphate and sodium stearate with the surfactant and urea. At the same time the combination of sodium sulphate and sodium stearate aids in slowing the rate of dissolution and increases the density of the bowl cleaner, it provides another salutary effect. That is, the amount of surfactant in the composition is reduced to as low as 8% to 20%, preferably about 10%, by weight, based on the weight of the composition, and this low level is achieved without reducing the bowl cleaning effect of the composition. Since the surfactant is the item of highest total cost in the bowl cleaner composition, the use of smaller amounts of surfactant than is customary, results in significant reduction in the raw material cost of the bowl cleaner composition. Additionally, because this composition allows for use of a liquid surfactant, manufacturing time and energy savings are realized when compared with compositions using waxy type surfactants which require more time and energy to prepare.

In summary, the toilet bowl cleaner of this invention comprising sodium sulphate, sodium stearate, surfactant and urea, water and dye, has the advantage of providing longer cleaner life, greater weight of composition per standard size container, effective bowl cleaning ability and reduced cost.

EXAMPLE 1

A solid toilet bowl cleaner composition was prepared by heating 10 g. of water to 130° F. This temperature was maintained and 23 g. of urea was added to the water with constant agitation until the urea dissolved. 1.3 g. of Neptune Blue Bra Powder supplied by GAF Corp. was added with agitation until dissolved. In a separate tank, 10 g. of nonionic surfactant available from GAF Corp. under the trademark Igepal CO-610 was combined with 0.4 g. methyl salicylate and 0.1 g. silicone and 0.4 g. sodium stearate was added and agitated until fully dispersed on the surfactant. This latter mixture of sodium stearate, surfactant, methyl salicylate and silicone was then combined with the mixture of urea and dye at a temperature of about 130° F. and agitated until fully mixed. The temperature of the mixture was raised to about 140° F. and 55 g. of sodium sulphate was added with constant agitation until uniformly mixed and then poured into 9 ounce plastic cups suitable for insertion in toilet bowls or tanks. The cups were found to contain about 13 ounces of toilet bowl cleaner.

Having described the invention, what is claimed is:

1. A toilet bowl cleaner comprising about 50% to about 60% sodium sulphate, about 17% to about 24% urea, about 8% to about 20% nonionic primary alcohol ethoxylate surfactant, about 8% to about 11% water, about 0.25% to about 2% sodium stearate, and about 1% to about 2% water soluble dye, said percentages being by weight, based on the weight of the composition.

2. The toilet bowl cleaner of claim 1 comprising about 55% sodium sulphate, about 23% urea, about 10% surfactant, about 10% water, about 0.4% sodium stearate, and about 1.3% dye, said percentages being by weight based on the weight of the composition.

3. The toilet bowl cleaner of claim 2 containing minor amounts of silicone and methyl salicylate.

* * * * *